Figure 1:
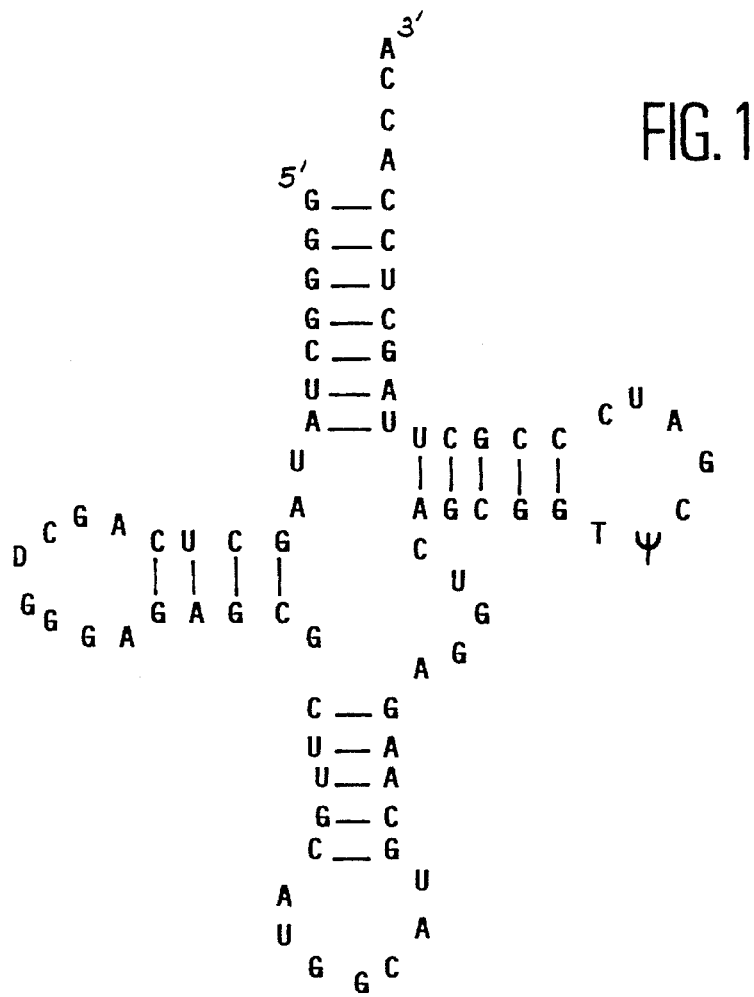

United States Patent [19]

Duplaa et al.

[11] Patent Number: 5,552,539
[45] Date of Patent: Sep. 3, 1996

[54] PROCESS FOR THE SYNTHESIS OF RIBONUCLEIC ACID (RNA) USING A NOVEL DEPROTECTION REAGENT

[75] Inventors: Anne-Marie Duplaa, Echirolles; Didier Gasparutto, Paris; Thierry Livache, Grenoble; Didier Molko, Tullins-Fures; Robert Teoule, Grenoble, all of France

[73] Assignees: Commissariat a l'Energie Atomique, Paris; CIS BIO International, Saclay, both of France

[21] Appl. No.: 211,424

[22] PCT Filed: Oct. 7, 1992

[86] PCT No.: PCT/FR92/00929

§ 371 Date: Jul. 26, 1994

§ 102(e) Date: Jul. 26, 1994

[87] PCT Pub. No.: WO93/07164

PCT Pub. Date: Apr. 15, 1993

[30] Foreign Application Priority Data

Oct. 8, 1991 [FR] France .................. 91 12357

[51] Int. Cl.⁶ .................. C07H 1/02; C07H 21/02
[52] U.S. Cl. .................. 536/25.31; 536/25.3
[58] Field of Search .................. 536/25.31, 25.3

[56] References Cited

FOREIGN PATENT DOCUMENTS

85/01051  3/1985  WIPO.
90/15814  12/1990  WIPO.

OTHER PUBLICATIONS

Derwent Publications Ltd., London, GB; Section Ch, Week 9119, 26 Jun. 1991, Class B, p. 21; JP,A,3 074 398 (Yuki Gosei Yakuhin) Mar. 28, 1991.

*Primary Examiner*—Gary L. Kunz
*Attorney, Agent, or Firm*—Oblon, Spivak, McClelland, Maier & Neustadt P.C.

[57] ABSTRACT

Process for RNA synthesis consisting in successively condensing necleosides for the formula (1) in which $R^1$ is a puric pyrimidic optionally protected base, $R^2$ is a leaving group such as the dimethoxytrityl radical, $R^3$ is a phosphorus-containing radical, for example, phosphoramidite and $R^4$ is a trialkylsilyl radical. The RNA obtained is then subjected to a protective treatment with a reagent of the formula (II), for example $N(C_2H_5)_3,3HF$, to eliminate $R^4$ protective groups of the 2' hydroxyl groups. Such reagent provides full deprotection in about ten hours, with an RNA of great length, for example, having more than 50 bases.

10 Claims, 4 Drawing Sheets

PROCESS FOR THE SYNTHESIS OF RIBONUCLEIC ACID (RNA) USING A NOVEL DEPROTECTION REAGENT

The present invention relates to a process for the synthesis of ribonucleic acid (RNA) using a deprotection agent making it possible to rapidly obtain a total deprotection of the hydroxyl groups in the 2'-position of the RNA.

For a number of years, processes for the synthesis of ribonucleic acid fragments have developed greatly as a result of the increasing interest in RNA, which plays an important part in numerous cellular processes.

These synthesis processes are similar to those used in the synthesis of deoxyribonucleic acid (DNA) and are e.g. described by Ogilvie et al in Proc. Natl. Acad. Sci., Vol. 85, pp. 5764–5768, August 1988 and by Gasparutto et al in Nucleosides & Nucleotides 9(8), pp. 1087–1098, 1990.

The starting product for this synthesis consists of ribonucleosides, whose hydroxyl in the 2'-position is protected by an appropriate group and which also has groups suitable for nucleotide synthesis and successive condensation takes place of these nucleoside derivatives in order to form ribonucleic acid.

Thus, in the aforementioned document Ogilvie et al used ribonucleoside derivatives in which the hydroxyl groups in the 2'-position are protected by the t-butyl-dimethyl silyl radical. After coupling all the nucleosides, a ribonucleic acid is consequently obtained, whose hydroxyls in the 2'-position are protected. Therefore, it is appropriate to carry out at the end of the operation a deprotection treatment in order to eliminate these 2'-hydroxyl protecting groups.

Hitherto, said deprotection has been performed by using as the deprotection reagent tetrabutyl ammonium fluoride in tetrahydrofuran as described in Glen Research Report, Vol. 4, No. 1, March 1991, RNA Synthesis—Problems in Deprotection. The deprotection of the hydroxyl function in the 2'-position of a nucleoside or nucleotide in free form carrying in the 2'-position a tert.-butyl dimethyl silyl (TBDMS) function takes place within a few minutes in a tetrabutyl ammonium fluoride. It is much more difficult in the case of an oligonucleotide carrying t-butyl dimethyl silyl in the 2'-position and takes hours (cf. FIG. 3, curve 5). It has been found that in the case of very long RNA fragments, e.g. more than 25 bases, the deprotection of the hydroxyl groups is not complete with this reagent, because there are at least 1 to 2% non-deprotected hydroxyl groups per base unit, i.e. each RNA molecule has at least one non-deprotected hydroxyl, which can be prejudicial to the biological activity of RNA, as has been indicated by Ogilvie.

The present invention relates to a process for the synthesis of ribonucleic acid (RNA), which makes it possible to totally and rapidly obtain the total deprotection of the hydroxyl groups in the 2'-position of the synthesized ribonucleic acid.

This process consists of a) successively condensing on a first nucleoside of formula:

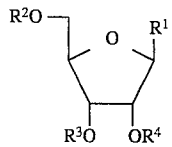

in which $R^1$ is a radical derived from a pyrimidic or puric base chosen from among the radicals of formula:

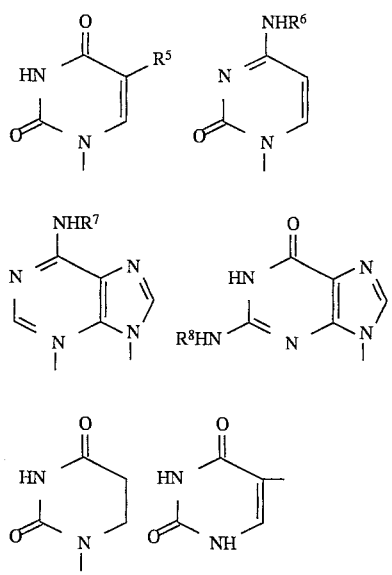

in which $R^5$ is H or $CH_3$ and $R^6$, $R^7$ and $R^8$ are hydrogen atoms or an acyl group protecting an exocyclic $NH_2$ group, $R^2$ is an unstable radical in an acid medium appropriate for nucleotide synthesis, $R^3$ is a solid support and $R^4$ is a trialkyl silyl radical, one or more identical or different nucleosides complying with the formula (I), in which $R^1$, $R^2$ and $R^4$ have the meanings given hereinbefore and $R^3$ is a phosphorus radical appropriate for nucleotide synthesis, in order to form a synthetic ribonucleic acid, whereof all the hydroxyl groups in the 2'-position are protected by $R^4$ and b) deprotecting all the hydroxyls in the 2'-position by treating the thus synthesized ribonucleic acid with a deprotection agent complying with the formula:

in which $R^9$ represents a straight or branched $C_1$ to $C_{10}$ alkyl radical, $R^{10}$ and $R^{11}$, which can be same or different represent H or a straight or branched $C_1$ to $C_{10}$ alkyl radical, which can be the same or different to $R^9$ and n is a number between 1 and 3, which may or may not be an integer.

In this process, successive condensation cycles are performed in order to couple the different nucleosides to one another using conventional methods, i.e. protocols and chemical reagents prescribed by the suppliers of RNA synthesizers.

To this end, the nucleoside of formula (I) used for each coupling comprises $R^2$ and $R^3$ radicals appropriate for the nucleotide synthesis and a group $R^1$ which depends on the base used When this base has an exocyclic $NH_2$ group, the latter is protected by appropriate protective groups generally used for nucleotide synthesis.

Appropriate protective groups are the acyl groups e.g. described in U.S. Pat. No. 4,980,460, Koster et al, Tetrahedron, Vol. 37, pp. 363–369, 1981, Wu et al, Nucleic Acids Research, Vol. 17, 9, 1989, pp. 3501–3517.

Preferably, in the invention, when the base is adenine or guanine, the protective group is constituted by the phenoxyacetyl group, i.e. $R^7$ and $R^8$ in the aforementioned formulas are preferably the phenoxyacetyl group.

When the base is cytosine, the protective group is preferably constituted by the acetyl group, i.e. $R^6$ in the aforementioned formula represents an acetyl group. In this case, it is also possible to use the isobutyryl or propionyl group.

For $R^2$ the unstable radicals in the acid medium which can be suitable are e.g.:

the trityl radicals complying with the formula:

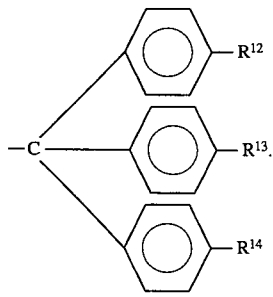

in which $R^{12}$, $R^{13}$ and $R^{14}$, which can be the same or different represent a hydrogen atom, an alkyl radical or an alkoxy radical, e.g. the monomethoxytrityl or dimethoxytrityl radical, pixyl radicals and 9-phenyl-xanthenyl radicals.

For $R^3$, the phosphorus radicals which can be used can e.g. be radicals of formula:

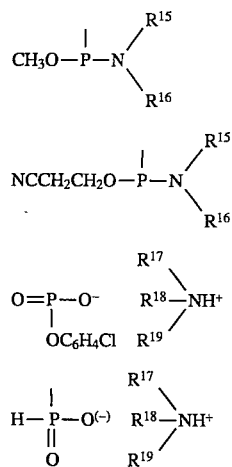

in which $R^{15}$, $R^{16}$, $R^{17}$, $R^{18}$ and $R^{19}$ are straight or branched alkyl radicals.

Preferably, in the process of the invention, use is made for $R^3$ of phosphoramidite groups of formula

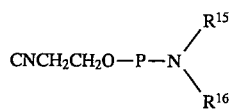

in which $R^{15}$ and $R^{16}$, which can be the same or different, are $C_1$ to $C_4$ alkyl radicals.

For example, $R^{15}$ can be the methyl radical and $R^{16}$ the ethyl radical, or $R^{15}$ and $R^{16}$ can both be isopropyl radicals.

The use of ethyl and methyl radicals for $R^{15}$ and $R^{16}$ is very interesting, because with them there is obtained a rapid coupling of the nucleotides (formation of the internucleotide bond in 3 minutes) with an excellent yield (98%) and less parasitic reactions. Moreover, the use of these radicals with the t-butyl-dimethyl silyl protective group in the 2'-position leads to stable nucleoside derivatives having an excellent reactivity for RNA synthesis, whereas these ethyl and methyl radicals give very unstable derivatives for DNA synthesis.

According to the process of the invention, after performing the successive condensation cycles for the nucleosides, the synthetic ribonucleic acid, whereof all the hydroxyls in the 2'-position are protected, is subject to a deprotection treatment using as the deprotection reagent the reagent complying with the formula:

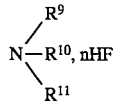

in which $R^9$ represents a straight or branched $C_1$ to $C_{10}$ alkyl radical, $R^{10}$ and $R^{11}$ which can be the same or different, represent H or a straight or branched, $C_1$ to $C_{10}$ alkyl radical and can be the same or different to $R^9$, and n is a number between 1 and 3, which may or may not be an integer.

As examples of such reagents reference can be made to $N(C_2H_5)_3$, 3HF; $N(CH_3)_3$, 2HF; $(CH_3)_2NH$, HF; isopropyl amine, HF, isopropyl amine 1.8 HF, diisopropyl amine 2 HF and diisopropyl amine 3 HF.

Preferably, in the invention, use is made of the deprotection reagent complying with the formula:

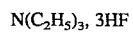

This known reagent has hitherto been used as a fluorination reagent for carbohydrates.

According to the invention, the use of this reagent for the deprotection of hydroxyls in the 2'-position of ribonucleic acid is very interesting, because it makes it possible to bring about a total deprotection of a ribonucleic acid of very great length in about ten hours. In addition, it can be used in the pure state and can then be easily eliminated by evaporation.

In general, the deprotection treatment is performed at ambient temperature for between 2 and 20 h.

It is also possible to use this reagent diluted in an organic solvent, e.g. in acetonitrile.

Other features and advantages of the invention can be better gathered from reading the following examples given in an illustrative and non-limitative manner and with reference to the attached drawings, wherein show:

FIG. 1 transfer RNA prepared in Example 1.

Figure 2:
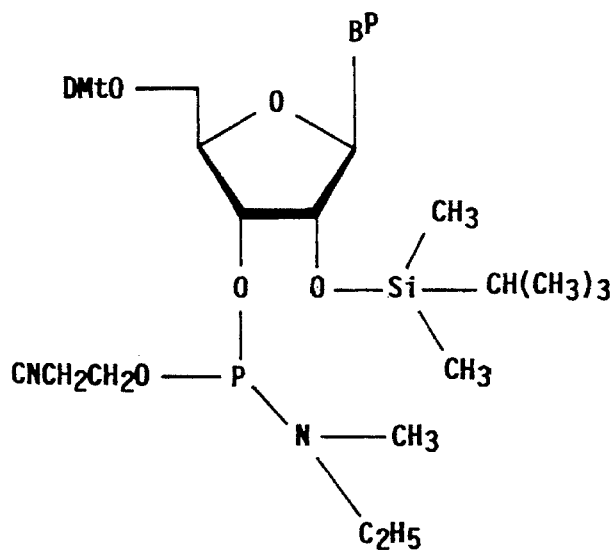

FIG. 2 phosphoramidites of ribonucleosides used for the synthesis of transfer RNA of Example 1.

Figure 3:
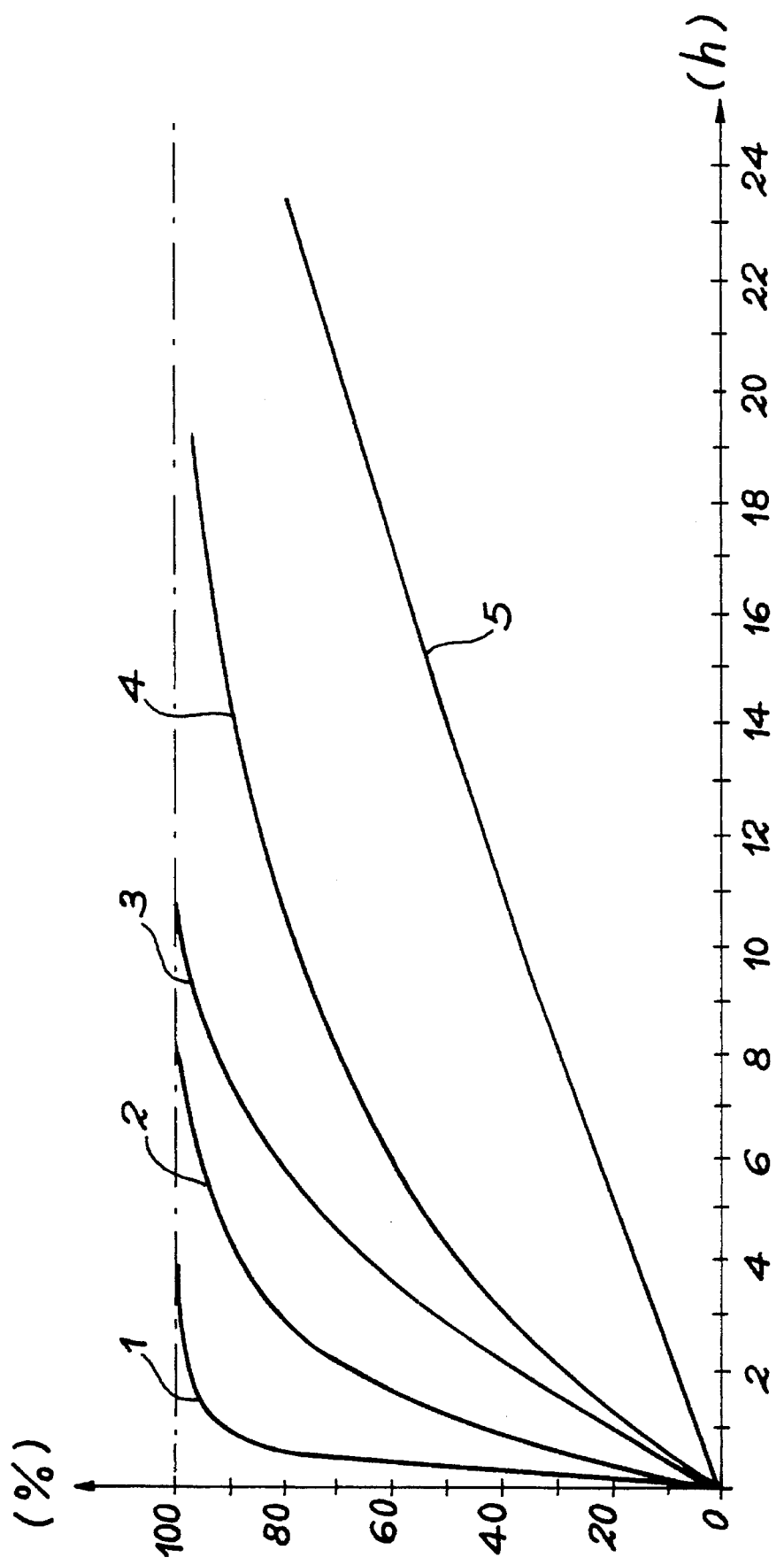

FIG. 3 a graph showing as a function of time (in h) the percentage deprotection of an oligonucleotide with 42 bases by different deprotection reagents.

FIGS. 4 to 9 chromatograms of oligonucleotides obtained in the case of high performance liquid chromatography.

EXAMPLE 1: Synthesis of Transfer Ribonucleic Acid t-RNA of alanine of *E. coli* $K_{12}$ This transfer RNA is illustrated by FIG. 1.

In order to carry out this synthesis, use was made of protected ribonucleoside phosphoramidites shown in FIG. 2. In FIG. 2 DMt represents the dimethoxytrityl group and $B^p$ the optionally protected, puric or pyrimidic base. In the case where the base is adenine or guanine, its exocyclic $NH_2$ group is protected by the phenoxyacetyl group and in the case of cytosine the exocyclic $NH_2$ group is protected by the acetyl group.

The base $B^p$ can also be uracil, thymine, 5,6-dihydrouracil and pseudouracil.

The successive condensation stages of the nucleosides are performed with a synthesizer using phenoxyacetic anhydride as the capping reagent. Synthesis is performed in the solid phase at a scale of 0.2 µ mole using a silica gel support with controlled pore dimensions.

Each condensation cycle involves the following stages:

detritylation: 2% trichloroacetic acid in $CH_2Cl_2$ for 90 min., washing: $CH_3CN$ for 2 min., condensation: nucleoside derivative+activating agent in anhydra $CH_3CN$ for 3 min., masking the hydroxyl functions which have not reacted in order to stop the elongation of the incomplete chains: mixture of phenoxyacetic anhydride and 1-methyl imidazole in anhydra $CH_3CN$ for 1 min., oxidation: 0.45% iodine in tetrahydrofuran/water/lutidine (89.5/10/0.5) for 45 sec., washing: $CH_3CN$ for 90 sec.

In each cycle, 45 nucleoside equivalents are used.

At the end of the operation, the oligonucleotide is freed from the support and the cyanoethyl group is hydrolyzed by treatment using a mixture of ethanol and an aqueous, concentrated ammonia solution (28% ammonia: ethanol, 3/1 by volume) for 2 h at ambient temperature.

The oligonucleotide is then heated at 55° C. for 1 h to eliminate the protective groups of the exocyclic $NH_2$ groups of the bases and then the solution is evaporated in vacuo, the residue being maintained at ambient temperature in 300 µl of deprotection agent $N(C_2H_5)_3$, 3HF in pure form (TEA, 3 HF) for 16 h.

The liquid phase is then evaporated to dryness and the salt is removed from the mixture of products, followed by the purification of the synthetic ribonucleic acid obtained by electrophoresis on 15% polyacrylamide gel (1.5 mm thick).

After marking or labelling the OH ends in the 3' or 5'-position by phosphorus 32, it is then checked that the ribonucleic acid obtained does in fact correspond to the RNA of FIG. 1, by carrying out a sequencing using enzymatic degradation processes.

In all cases, the structure of the transfer ribonucleic acid is in accordance with the sequence given in FIG. 1.

The structure of the synthetic ribonucleic acid obtained in this way is then checked by carrying out on a small amount of said RNA a hybridization of its 3' end with a complementary oligodeoxynucleotide having a length of 16 bases and this is copied with inverse transcriptase. After PCR amplification, the two DNA chains can be sequenced and correspond perfectly to the expected sequence.

EXAMPLE 2

In this example, evaluation takes place of the deprotection level according to the invention on an oligonucleotide $dT_{21}rUdT_{20}$, serving as a model, which is an oligonucleotide having a DNA chain, in which is included a single ribonucleotide rU protected by a tert. butyl dimethyl silyl group.

In order to synthesize this oligonucleotide $dT_{21}rUdT_{20}$, the same operating procedure as in Example 1 is followed, except that the starting nucleosides used are constituted by the compound of FIG. 2 in which $B^P$ represents thymine and in which

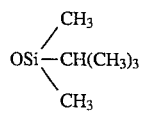

is replaced by H, and the compound of FIG. 2 in which $B^P$ represents uracil.

After synthesis, deprotection is carried out for different times and after each deprotection treatment, the deprotection level is determined by separating the product obtained on an inverse phase $C_{18}$ column, which makes it possible to separate the completely deprotected fragments from their homologs still carrying the tert. butyl dimethyl silyl group.

The results obtained are represented by curve (1) in FIG. 3, which reveals that there is a 100% deprotection level in 4 h.

EXAMPLE 3

The same operating procedure as in Example 2 is followed in order to prepare the oligonucleotide $dT_{21}$-rU-$dT_{20}$, but deprotection is carried out using a mixture of the reagent according to the invention (TEA, 3HF) and acetonitrile with a volume ratio of 1/1. The results obtained are represented by curve 2 in FIG. 3. FIG. 3 shows that as a result of the dilution of the deprotection reagent according to the invention by acetonitrile, a complete deprotection is obtained after 8 h.

COMPARATIVE EXAMPLE 1

In this example, the operating procedure used in Example 2 is followed for preparing the oligonucleotide $dT_{21}$-rU-$dT_{20}$, but deprotection is carried out using the prior art deprotection reagent, namely tetrabutyl ammonium trihydrate fluoride (TBAF, $3H_2O$) at a rate of 1 mole/l in dimethyl sulphoxide.

The results obtained are represented by curve 3 in FIG. 3. Thus, with the prior art reagent, 11 h are needed to obtain total deprotection.

COMPARATIVE EXAMPLE 2

This example follows the same operating procedure as in Example 2 for preparing the oligonucleotide $dT_{21}$-rU-$dT_{20}$, but for deprotection use is made of a 1 mole/l solution of TBAF, $3H_2O$ in dimethyl formamide.

The results obtained are represented by curve 4 in FIG. 3. In this case it is necessary to wait for 24 h in order to obtain total deprotection.

COMPARATIVE EXAMPLE 3

This example follows the same operating procedure as in Example 2 for preparing oligonucleotide $dT_{21}$-rU-$dT_{20}$ and deprotection is brought about by using a 1 mole/l solution of TBAF, $3H_2O$ in tetrahydrofuran (THF).

The results obtained are represented by curve 5 in FIG. 3. FIG. 3 shows that it is impossible to obtain a total deprotection with tetrabutyl ammonium fluoride in THF, which is the presently used reagent.

EXAMPLE 4

This example follows the same operating procedure as in Example 1 for preparing an oligonucleotide 18 bases long and having the following sequence:

5'UTUACUAUCUAUCUCCCAA3'

Following the elimination of the protective groups of the exocyclic $NH_2$ groups of the bases in an ammoniacal medium, approximately 40 µg, i.e. 2 absorption units at 260 nm (20D) of the silylated oligonucleotide are treated in an Eppendorf microtube by 60 µl of the deprotection reagent $N(C_2H_5)_3$, 3HF (TEA, 3HF) for 20 h at ambient temperature. Aliquot portions of the reaction mixture are sampled in order to follow the evolution of the reaction, prior to the reaction with TEA, 3HF, after 4 h of reaction and after 20 h of reaction. After sampling, each aliquot portion is neutralized by 4 volumes of triethyl ammonium acetate TEAA (pH 7.0, 25 mM) and then analysis takes place by high performance liquid chromatography in ion exchange using a mono Q column (LKB) and eluting the column by a gradient of 0 to 1% KCl in 40 min. in a $KH_2PO_4$ buffer (pH 6.0). In the case of the sampling performed after 20 h of reaction, part of the latter is analysed in the same way as the previous samples following neutralization, whereas the other part undergoes salt removal after neutralization by TEAA, on a Sephadex G25 column (Pharmacia NAP 10) and then analysed by high performance liquid chromatography (HPLC) in the same way. The salt removal makes it possible to eliminate the parasitic peaks produced by the TEA, 3HF mixture.

Figure 4:
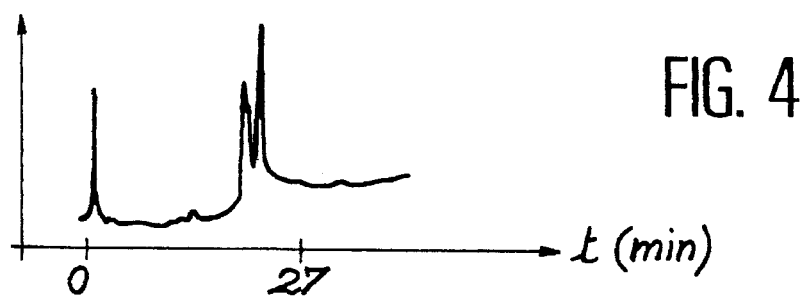
Figure 5:
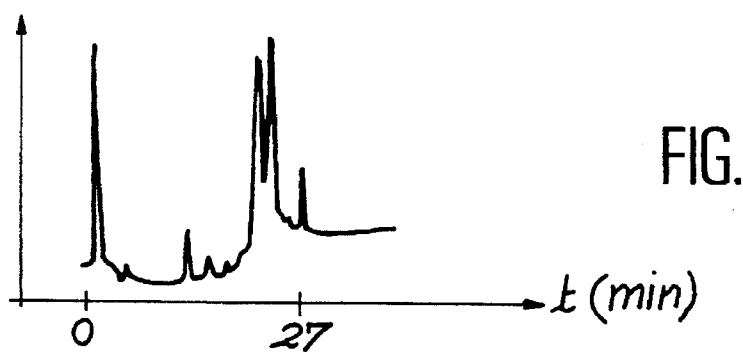
Figure 6:
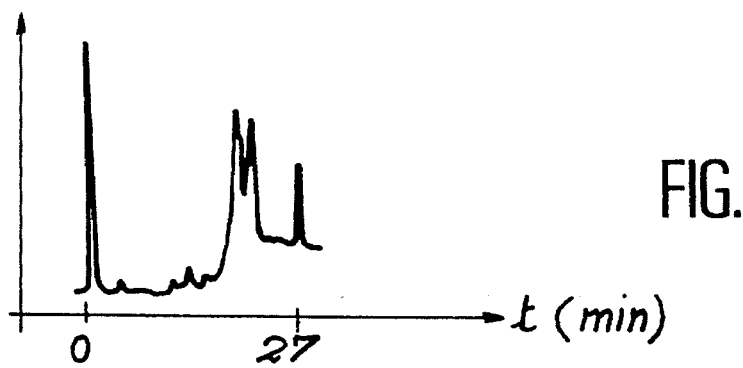
Figure 7:
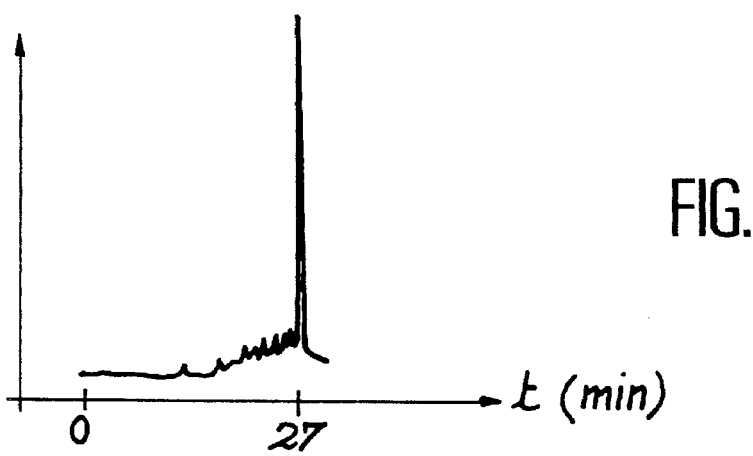

The results obtained are given in FIGS. 4 to 7. FIG. 4 is the chromatogram obtained at time 0, i.e. before the reaction with TEA, 3HF. FIG. 5 is the chromatogram obtained after 4 h reaction. FIG. 6 is the chromatogram obtained after 20 h reaction. FIG. 7 is the chromatogram obtained after 20 h reaction on subjecting the sampledproduct to salt removal. In all cases, injection takes place of 1 µl of product, except in the case of FIG. 7 where 2.5 µl of product are injected.

It can be seen on these chromatograms that the deprotected oligonucleotide appears after 4 h reaction (chromatograms of FIGS. 5,6 and 7) for a retention time $t_R$ of 27 min. A pronounced deprotection up to 20 h only leads to a slight yield improvement and there is very little supplementary degradation (cf. FIG. 6).

Following salt removal (FIG. 7), the salt-removed product has the purity of crude oligoribonucleotide. The incomplete sequences are clearly visible on the chromatogram.

Thus, the oligonucleotide obtained after deprotection followed by salt removal is very pure and a high yield is obtained.

EXAMPLE 5

In this example there is a check that the TEA-3HF product used for the deprotection does not degrade the oligoribonucleotides produced by studying the stability of a natural transfer RNA in the presence of TEA-3HF.

To this end, use is made of transfer RNA of *E. coli* specific of formyl-methionine (Boehringer), which contains numerous modified bases such as 4-thiouridine, 5-methyluridine, dihydrouridine, pseudouridine, 7-methylguanosine and 2'0-methylcytidine.

Figure 8:
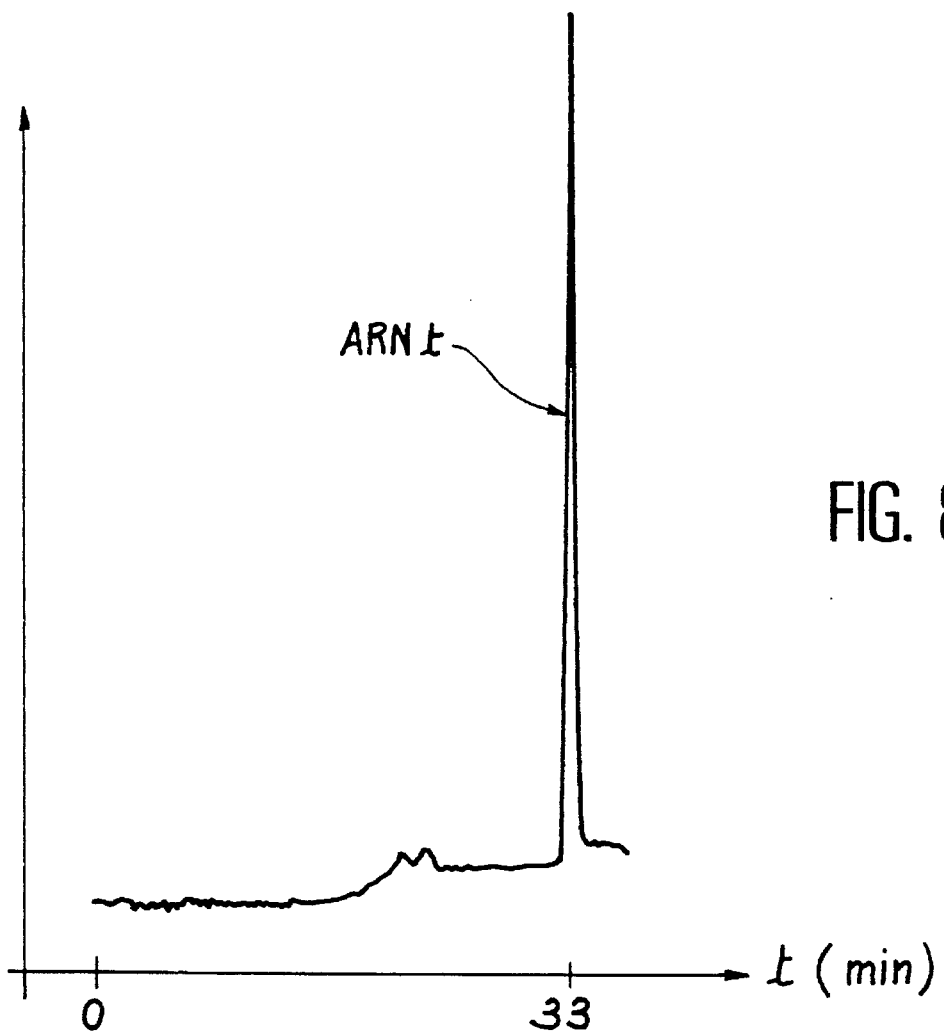

In order to test the stability of this $RNA_f$, 40 µg of $RNA_f$ (2 OD) are introduced into 60 µl of TEA-3HF and vigorous stirring takes place by means of a vortex for 2 h. The product is then left in this medium for 20 h at ambient temperature and then neutralization takes place by 4 volumes of TEAA, 25 mM, pH 7.0 and then the product is subject to salt removal on a Pharmacia NAP-10 column. 1.8 OD of this product (i.e. 90%) are recovered, followed by analysis by ion exchange high performance liquid chromatography, as in Example 4. FIG. 8 is the chromatogram obtained by injecting 0.025 OD onto the column.

Figure 9:
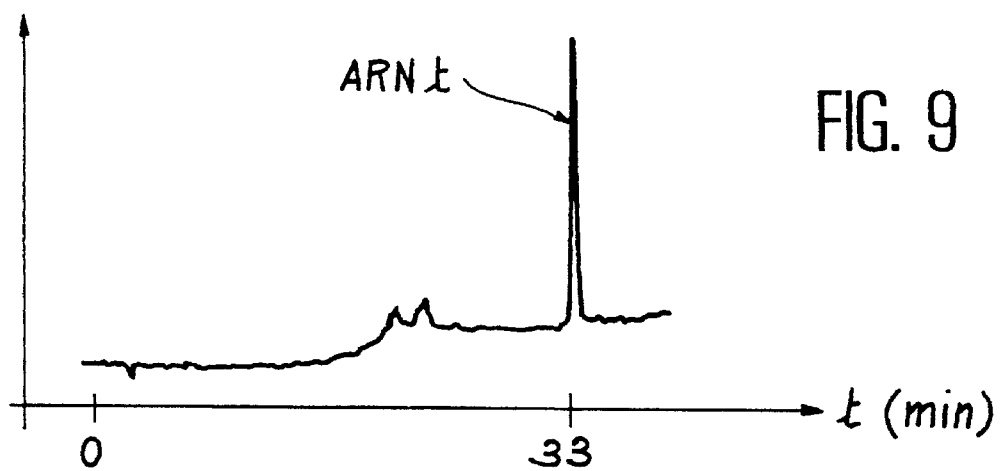

FIG. 9 shows for comparison purposes the chromatogram obtained with the same natural, untreated $RNA_f$, when 0.01 OD is injected onto an identical column.

On comparing these two chromatograms it can be seen that the retention times are strictly identical and that no incomplete sequence product is visible on the chromatogram of FIG. 8.

Consequently, the use of the deprotection reagent TEA-3HF for 20 h at ambient temperature leads to no degradation of the natural $RNA_f$, which contains modified bases and which are known to be fragile.

We claim:

1. In a process for synthesizing RNA comprising:

a) successively condensing on a first protected nucleoside and having formula I:

one or more protected nucleosides of Formula I having the same or different heterocyclic bases in order to form a protected synthetic ribonucleic acid molecule wherein all of the hydroxyl groups in the 2'-position are protected by $R^4$, wherein $R^1$ is a heterocyclic radical selected from the group consisting of the following structures:

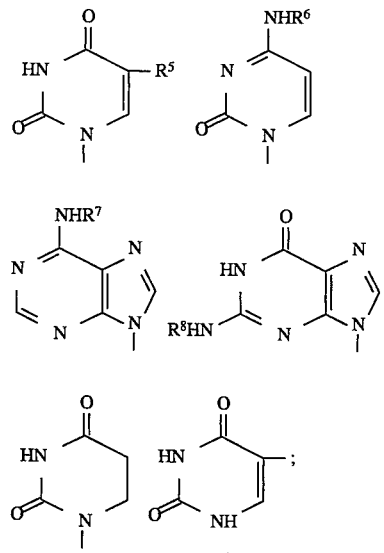

$R^2$ is an acid-labile protecting group;

$R^3$ is a solid support or a phosphorus radical appropriate for oligonucleotide synthesis;

$R^4$ is trialkyl silyl;

$R^5$ is hydrogen or methyl; and $R^6$, $R^7$, and $R^8$ are hydrogen or an acyl group protecting an exocyclic amino group, and b) deprotecting all of the 2'-hydroxyls of the protected RNA molecule by treating said RNA with a deprotection reagent, the improvement comprising using a deprotection reagent of Formula II:

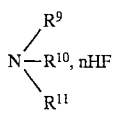

wherein $R^9$ is straight or branched $C_1$–$C_{10}$ alkyl;

$R^{10}$ and $R^{11}$ are the same or different and are hydrogen, or a straight or branched $C_1$–$C_{10}$ alkyl which may be the same as or different than $R^9$; and n is a number, which may or may not be an integer, between and including 1 and 3.

2. The process of claim 1 wherein the deprotection reagent is $N(C_2H_5)_3$, 3HF.

3. The process of claims 1 or 10 wherein the deprotection is performed at ambient temperature for 140 min.

4. The process of claims 1 or 10 wherein $R^4$ is t-butyldimethylsilyl.

5. The process of claims 1 or 2 wherein $R^3$ has the following formula:

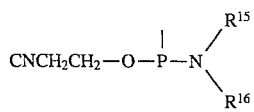

wherein $R^{15}$ and $R^{16}$ are the same or different and are $C_1$–$C_4$ alkyl.

6. The process of claim 5 wherein $R^{15}$ is methyl and $R^{16}$ is ethyl.

7. The process of claim 5 wherein $R^{15}$ and $R^{16}$ are isopropyl.

8. The process of claims 1 or 2, wherein $R^2$ is dimethoxytrityl.

9. A process for deprotecting the 2'-hydroxyls of an RNA molecule wherein the 2'-hydroxyls have been protected with a trialkyl silyl group, which comprises treating said RNA molecule with a deprotection reagent of Formula II:

wherein $R^9$ is straight or branched $C_1$–$C_{10}$ alkyl;

$R^{10}$ and $R^{11}$ are the same or different and are hydrogen, or a straight or branched $C_1$–$C_{10}$ alkyl which may be the same as or different than $R^9$; and n is a number, which may or may not be an integer, between and including 1 and 3.

10. The process of claim 9, wherein the trialkyl silyl group is a t-butyldimethylsilyl group.

* * * * *